US012773179B2

(12) United States Patent
Brown

(10) Patent No.: US 12,773,179 B2
(45) Date of Patent: Oct. 27, 2026

(54) DETECTION DEVICE FOR DETERMINING A POSITION OF A PHANTOM

(71) Applicant: Elekta Limited, Crawley (GB)

(72) Inventor: Kevin Brown, Crawley (GB)

(73) Assignee: Elekta Limited, Crawley (GB)

( * ) Notice: Subject to any disclaimer, the term of this patent is extended or adjusted under 35 U.S.C. 154(b) by 534 days.

(21) Appl. No.: 18/264,669

(22) PCT Filed: Feb. 9, 2022

(86) PCT No.: PCT/EP2022/053161
§ 371 (c)(1),
(2) Date: Aug. 8, 2023

(87) PCT Pub. No.: WO2022/171694
PCT Pub. Date: Aug. 18, 2022

(65) Prior Publication Data

US 2024/0115228 A1 Apr. 11, 2024

(30) Foreign Application Priority Data

Feb. 10, 2021 (GB) ..................................... 2101852

(51) Int. Cl.
*A61B 6/58* (2024.01)
*A61N 5/10* (2006.01)

(52) U.S. Cl.
CPC ............ *A61B 6/584* (2013.01); *A61N 5/1075* (2013.01); *A61N 2005/1076* (2013.01)

(58) Field of Classification Search
None
See application file for complete search history.

(56) References Cited

U.S. PATENT DOCUMENTS

2005/0117708 A1* 6/2005 Cho ....................... A61B 6/027
378/164
2007/0071176 A1 3/2007 Main et al.
(Continued)

FOREIGN PATENT DOCUMENTS

EP 2422847 A1 2/2012
WO WO-2016170115 A1 10/2016

OTHER PUBLICATIONS

"International Application Serial No. PCT/EP2022/053161, International Search Report dated May 19, 2022", (May 19, 2022), 4 pgs.
(Continued)

*Primary Examiner* — Hoon K Song
(74) *Attorney, Agent, or Firm* — Schwegman Lundberg & Woessner, P.A.

(57) ABSTRACT

A detection device for a radiotherapy apparatus is described. The detection device comprises an arrangement of detectors comprising a plurality of radiation detectors, each detector arranged and configured to detect a projection of a feature of a phantom at the respective detector when a beam of radiation is applied to the phantom, and output a measurement value based on the detected projection. The detection device further comprises a controller configured to receive the measurement values from the plurality of detectors and determine a position of the phantom in a first coordinate system based on the received measurement values.

24 Claims, 10 Drawing Sheets

(56) References Cited

U.S. PATENT DOCUMENTS

| | | | | |
|---|---|---|---|---|
| 2008/0217561 | A1* | 9/2008 | Mackie | A61N 5/1075<br>250/491.1 |
| 2013/0229495 | A1* | 9/2013 | Bani-Hashemi | A61B 6/582<br>348/46 |
| 2017/0319156 | A1* | 11/2017 | Hong | A61B 6/5205 |
| 2019/0054322 | A1* | 2/2019 | Yang | A61N 5/1081 |
| 2019/0369268 | A1 | 12/2019 | Casse et al. | |

OTHER PUBLICATIONS

"International Application Serial No. PCT/EP2022/053161, Written Opinion dated May 19, 2022", (May 19, 2022), 7 pgs.
"United Kingdom Application Serial No. 12101852.8, Examination Report dated Jun. 30, 2021", (Jun. 30, 2021), 6 pgs.
"European Application No. 22 706 268.4, Communication pursuant to Article 94(3) EPC dated Mar. 17, 2025", (Mar. 17, 2025), 6 pgs.

* cited by examiner

DETECTION DEVICE FOR DETERMINING A POSITION OF A PHANTOM

PRIORITY APPLICATIONS

This application is a U.S. National Stage Filing under 35 U.S.C. § 371 from International Application No. PCT/EP2022/053161, filed on Feb. 9, 2022, and published as WO2022/171694 on Aug. 18, 2022, which claims the benefit of priority to British Application No. 2101852.8, filed on Feb. 10, 2021; the benefit of priority of each of which is hereby claimed herein, and which applications and publication are hereby incorporated herein by reference in their entireties.

The present disclosure relates to radiotherapy systems, and in particular to methods and devices for performing quality assurance (QA) in radiotherapy.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

Radiotherapy devices may have portal imaging capabilities. Such a radiotherapy device may comprise an integrated electronic portal imaging device (EPID). It is known to utilise integrated imaging devices, such as amorphous silicon image detectors, to perform tasks such as confirmation of the patient setup relative to the radiation beam and portal dosimetry (the measurement of the exit dose from a patient and subsequent reconstruction of delivered dose on the patient geometry). These detectors can also be used for checking the outputs of a radiotherapy device to provide quality assurance (QA) in relation to the device.

However, many of these integrated portal imaging devices are optimised for patient imaging using a megavoltage (MV) beam. They are also designed for high quantum efficiency to reduce radiation dose to the patient, which increases cost. The result is that a typical EPID detecting panel is large, has a very high sensitivity across its width and length, and is optimised to produce high resolution patient images. Such prior detecting panels are by necessity expensive, an issue which is compounded by the fact that, due to their presence in the path of the damaging high energy MV beam during treatment, they do not have a long operational lifetime and must be replaced often.

It would be advantageous to provide a radiotherapy apparatus with a radiation detector system which is optimised for performance and cost in relation to the task of performing quality assurance (QA) in relation to the apparatus.

The present invention seeks to address this, and other disadvantages encountered in the prior art, by providing an improved radiotherapy apparatus with a radiation detector system.

SUMMARY

Aspects and features of the present invention are described in the accompanying claims.

According to a first aspect, there is provided a detection device for a radiotherapy apparatus, the detection device comprising: an arrangement of detectors comprising a plurality of radiation detectors, each detector arranged and configured to: detect a projection of a feature of a phantom at the respective detector when a beam of radiation is applied to the phantom; output a measurement value based on the detected projection; and a controller configured to: receive the measurement values from the plurality of detectors; and determine a position of the phantom in a first coordinate system based on the received measurement values.

The position of the phantom may be determined based on a predetermined relationship between phantom position and measurement values from the plurality of radiation detectors.

The predetermined relationship may be based on a calibration between phantom position and measurement values.

Each detector may correspond to a single pixel.

The measurement value may be a measurement of an overlap of the feature of the phantom on the respective detector.

The feature may be an edge of a shadow cast by the phantom.

The detectors may be arranged such that each detector can detect a projected feature of the phantom when the phantom is at an isocentre of the radiotherapy apparatus.

The detectors may be arranged with a pitch that corresponds to a distance between the projected features of the phantom.

The detectors may be arranged around a non-detecting region of the detection device.

The non-detecting region may be substantially aligned with a projected isocentre of the radiotherapy apparatus.

A first pair of the detectors may be arranged to detect opposing projected features of the phantom, and the controller may be configured to determine the position of the phantom in a first dimension of the first coordinate system based on the measurements from the first pair of detectors.

A second pair of the detectors may be arranged to detect opposing projected features of the phantom, and the controller may be configured to determine the position of the phantom in a second dimension of the first coordinate system based on the measurements from the second pair of detectors.

The position of each detector may be configurable in order to complement phantoms having different physical characteristics.

The controller may be configured to determine a position of the phantom in a second coordinate system using an imaging apparatus, and to compare the phantom position in the first coordinate system to the phantom position in the second coordinate system.

According to another aspect, there is provided a radiotherapy apparatus comprising: a radiation source configured to emit the beam of radiation; and a detection device according to any preceding aspect.

According to another aspect, there is provided a kit comprising: a detection device according to any preceding aspect; and a complementary phantom configured such that each detector of the detection device can detect a projected feature of the phantom when the phantom is at an isocentre of the radiotherapy apparatus and a beam of radiation is applied to the phantom.

According to another aspect, there is provided a method of determining a position of a phantom in a radiotherapy system, the method comprising: receiving a measurement value, from each of a plurality of radiation detectors of an arrangement of detectors, of a projection of a feature of the phantom at the respective detector when a beam of radiation is applied to the phantom, each detector being arranged to detect the respective projection of the feature of the phantom when the beam of radiation is applied to the phantom; and determining the position of the phantom in a first coordinate system based on the received measurement values.

The position of the phantom may be determined based on a predetermined relationship between phantom position and measurement values from the plurality of radiation detectors.

The predetermined relationship may be based on a calibration between phantom position and measurement values.

Each measurement value may correspond to a single pixel.

The method may further comprise determining a position of the phantom in a second coordinate system using an imaging apparatus, and comparing the phantom position in the first coordinate system to the phantom position in the second coordinate system.

The measurement value may be a measurement of an overlap of the feature of the phantom on the respective detector.

The feature may be an edge of a shadow cast by the phantom.

According to another aspect, there is provided a computer-readable medium that stores instructions which, when executed by one or more processors of a computer device, cause the computer device to perform a method according to any aspect above.

FIGURES

Specific embodiments are now described, by way of example only, with reference to the drawings, in which.

Figure 3A:
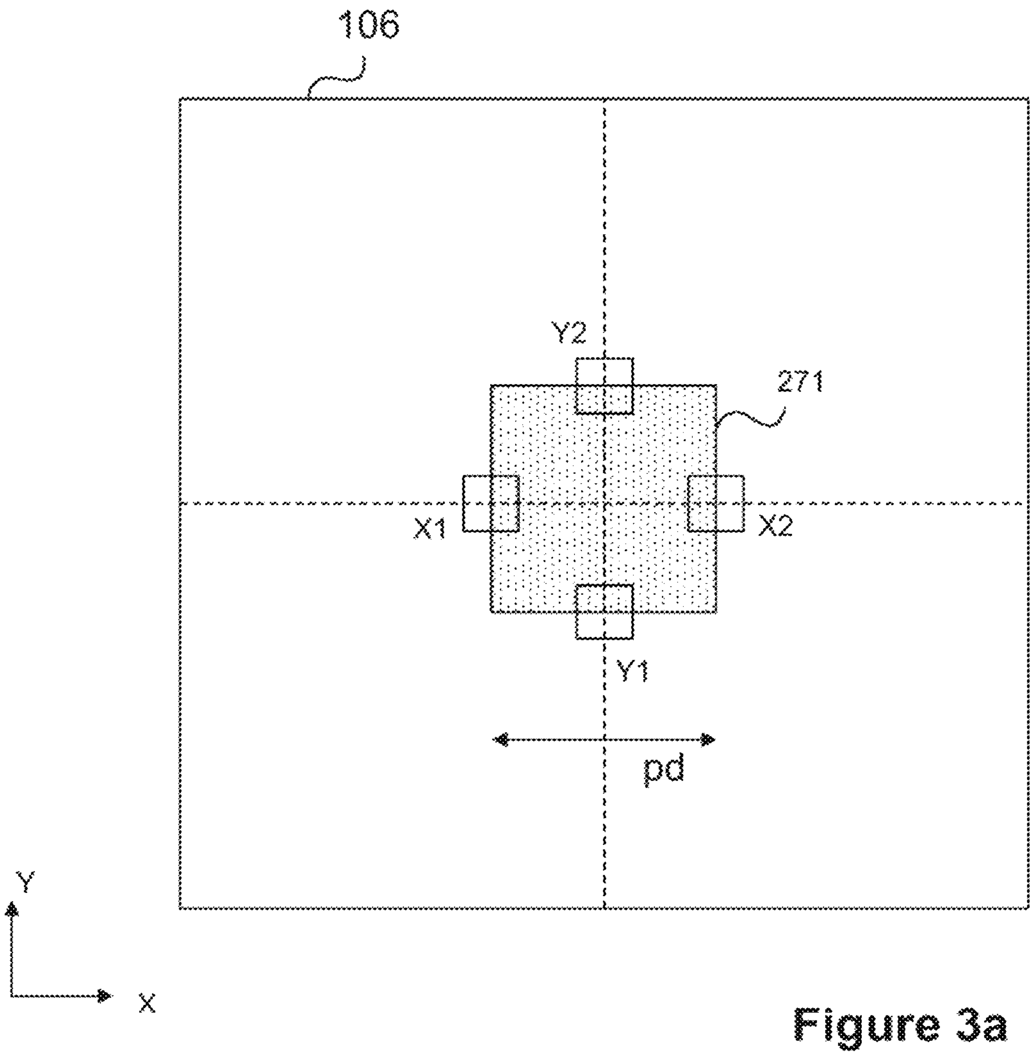
Figure 3B:
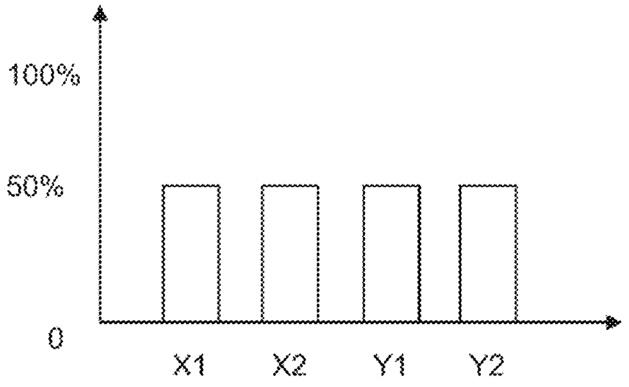
Figure 4A:
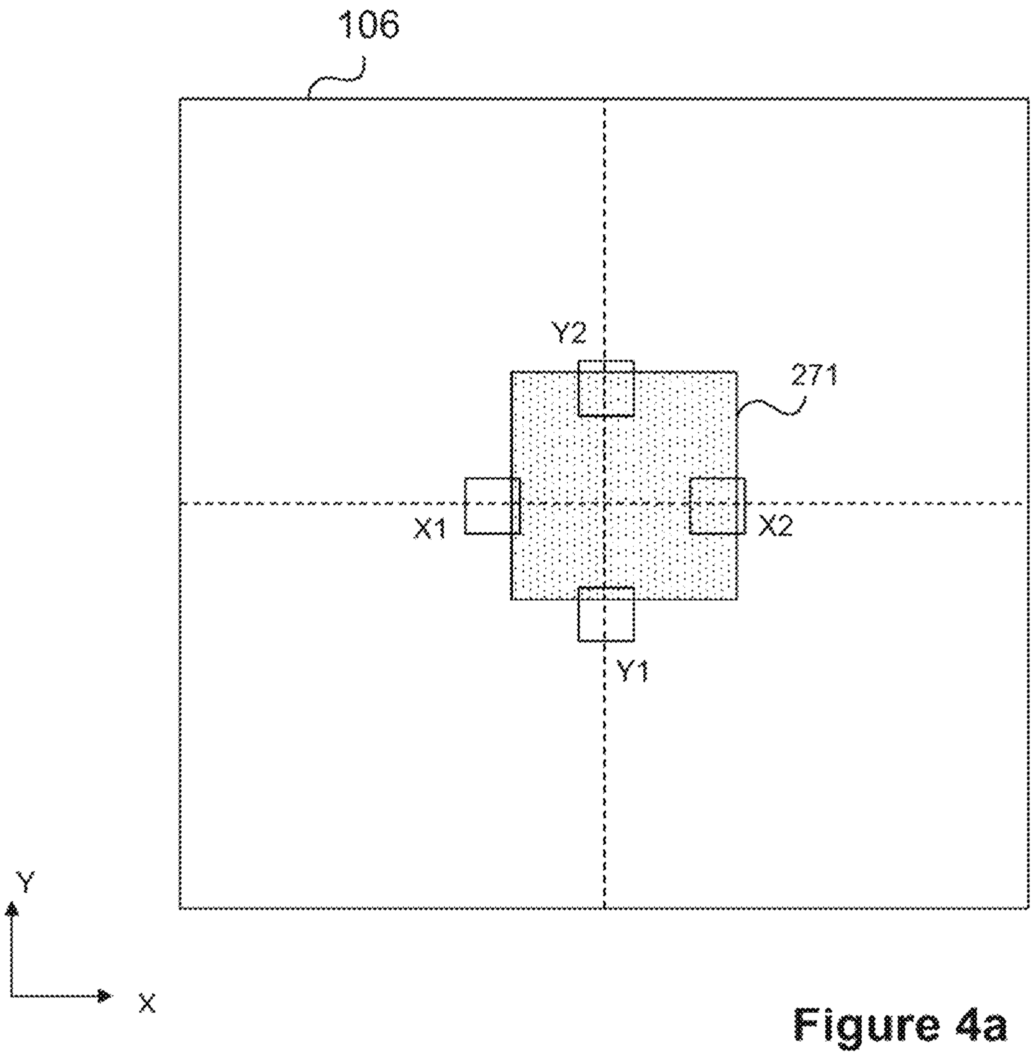
Figure 4B:
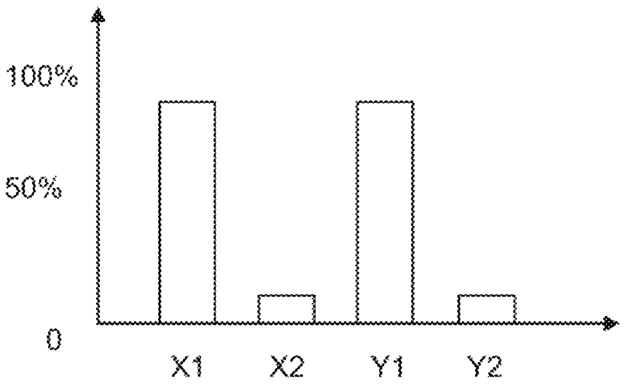
Figure 5:
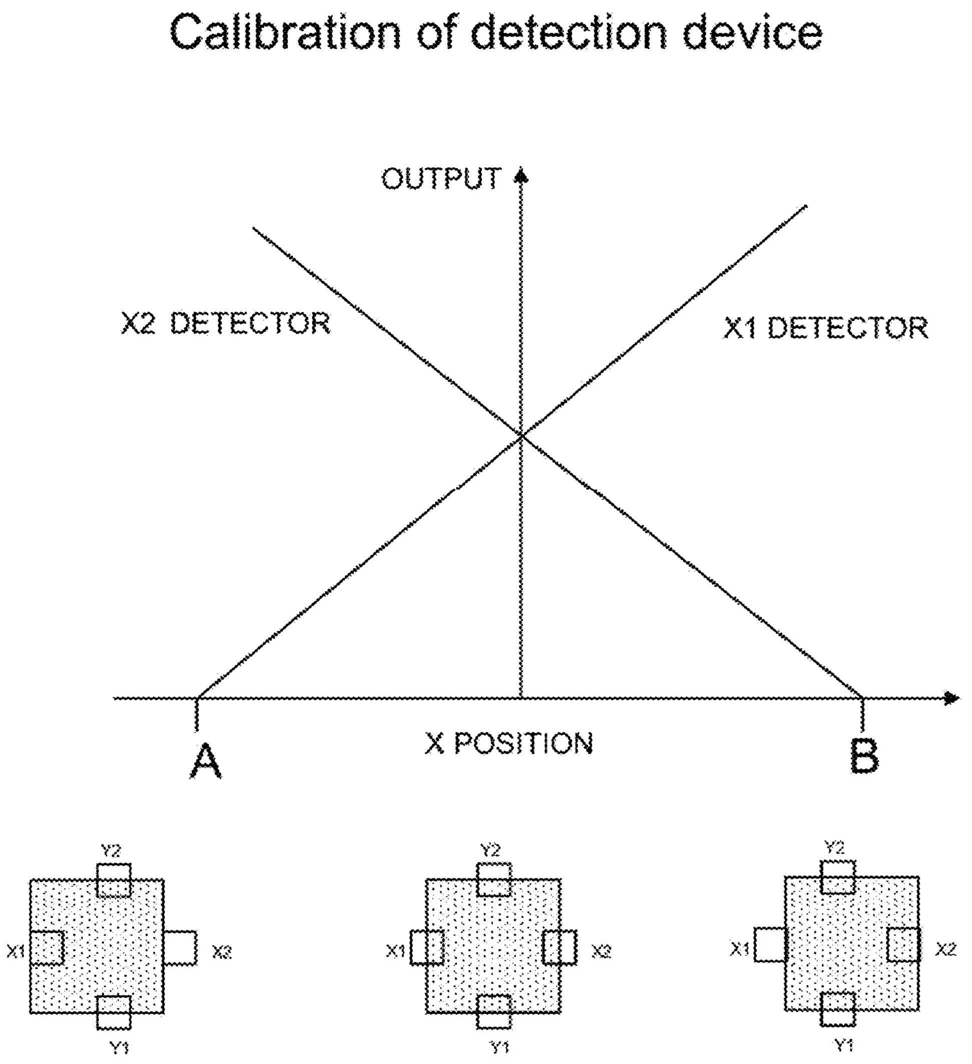
Figure 6:
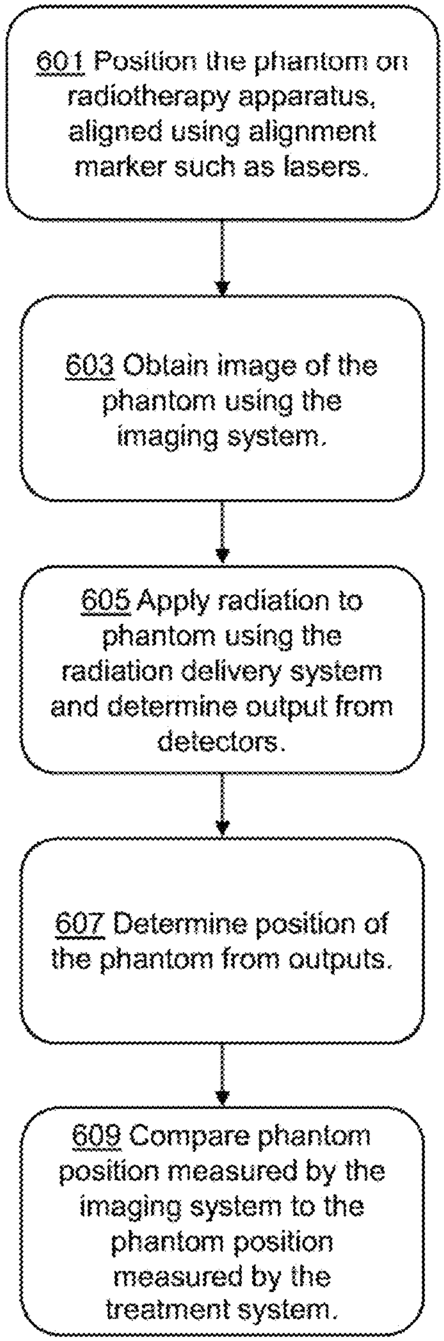
Figure 7:
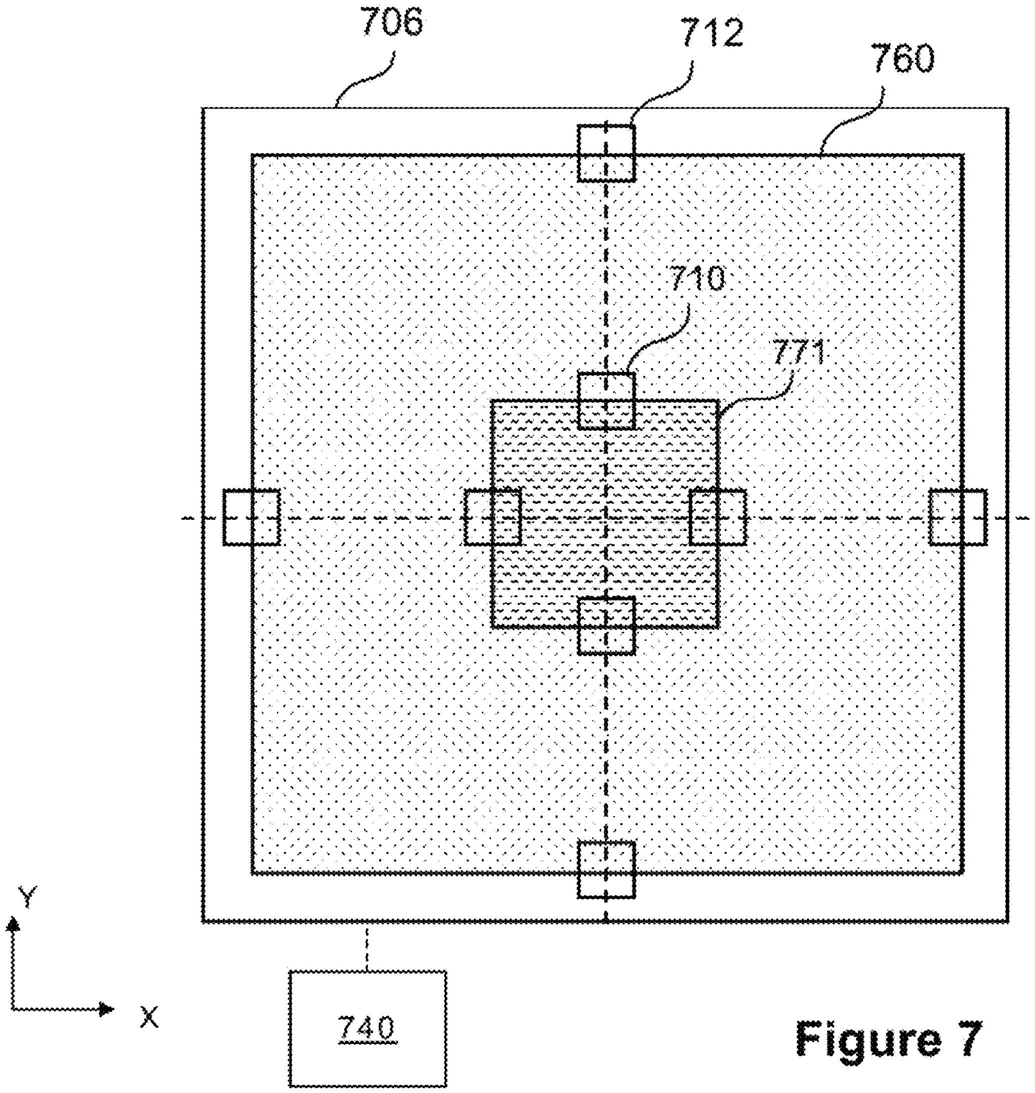
Figure 8A:
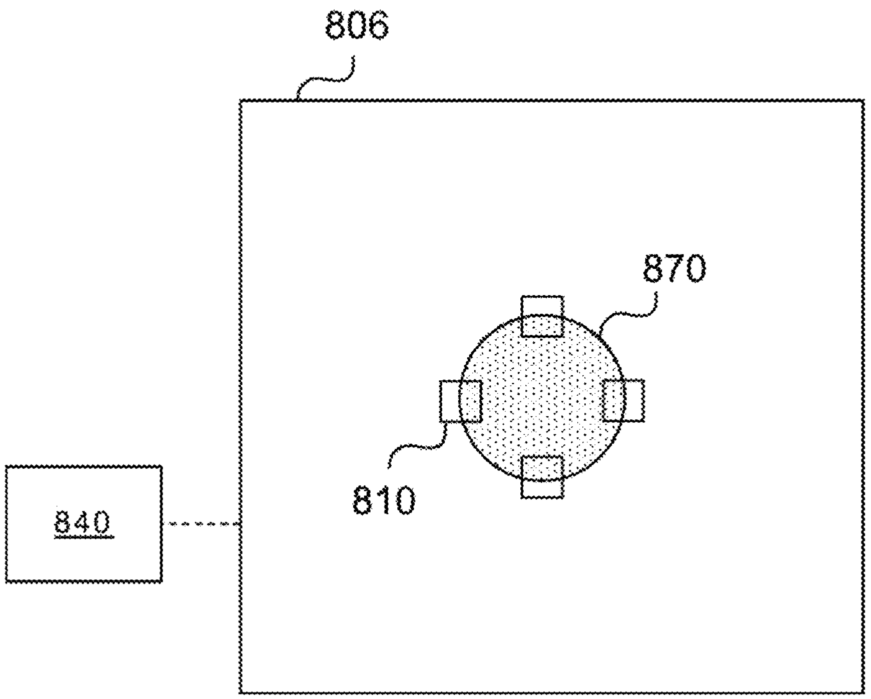
Figure 8B:
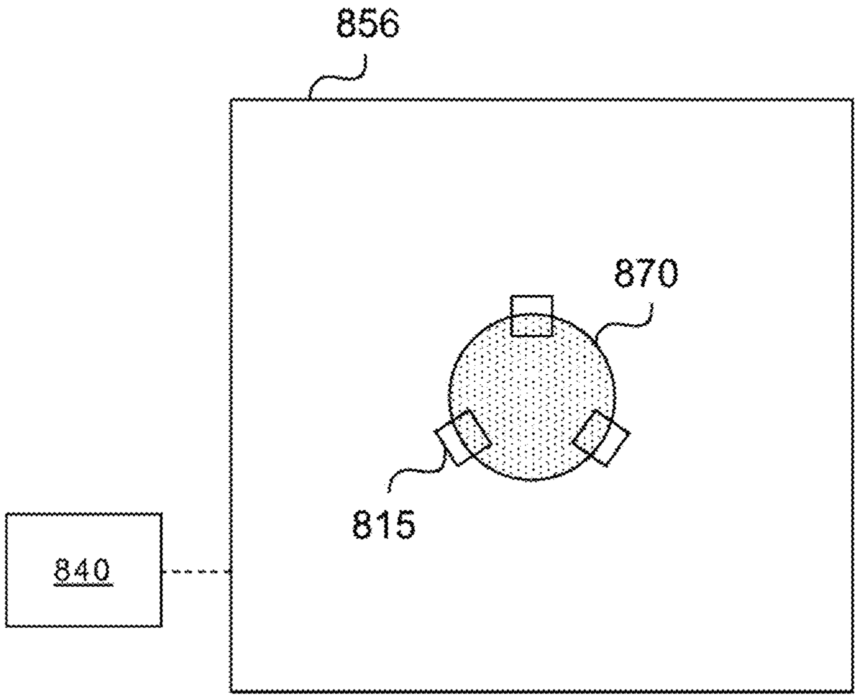
Figure 9A:
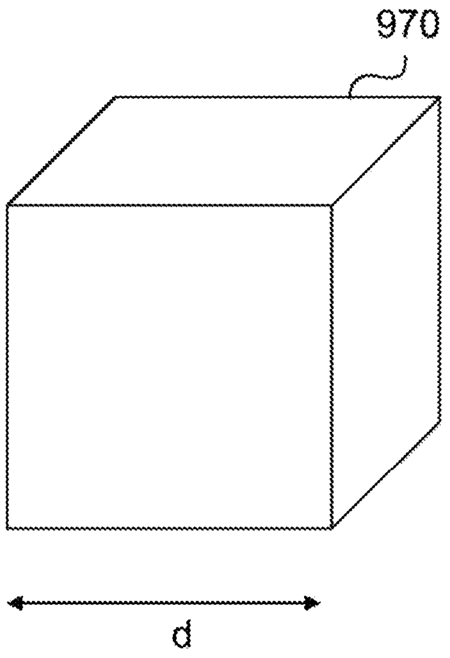
Figure 9B:
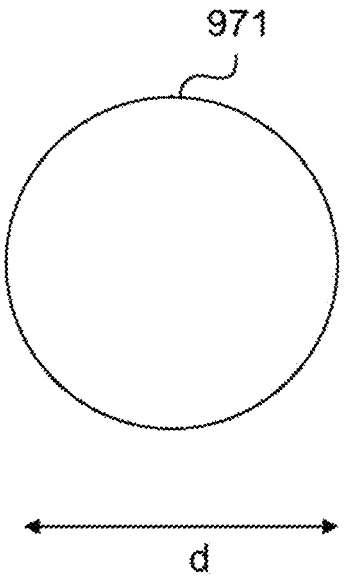
Figure 9C:
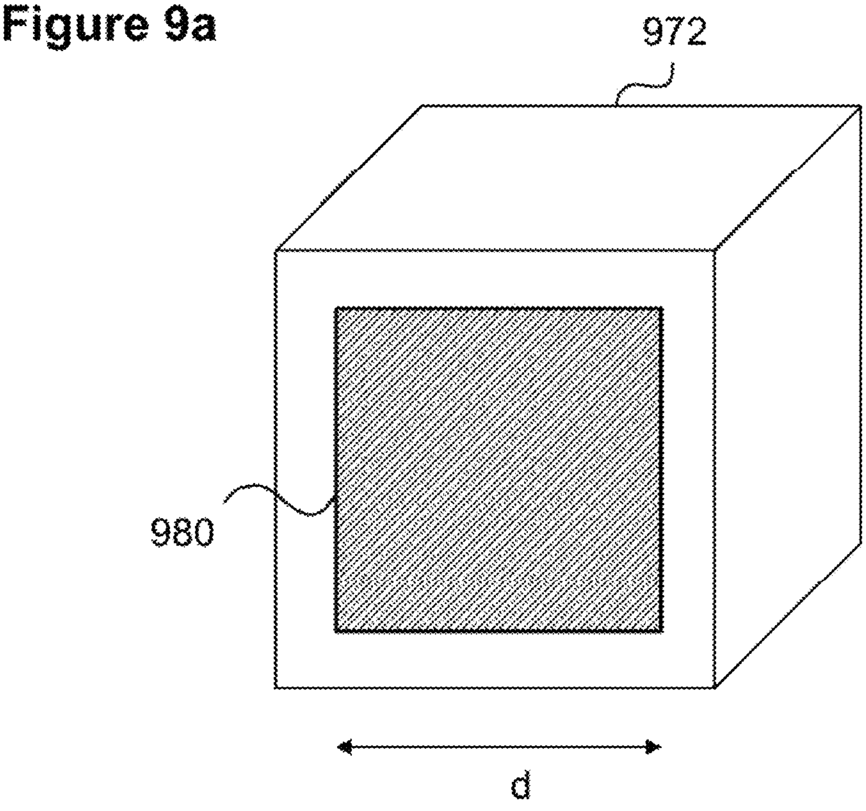

FIGS. 3*a* and 3*b* illustrate detection device in use;

FIGS. 4*a* and 4*b* illustrate detection device in use;

FIG. 5 is a graph showing exemplary outputs from detectors of the detection device;

FIG. 6 sets out simplified method steps of an exemplary geometric accuracy QA test;

FIG. 7 illustrates an embodiment of a detection device which includes additional detectors for detecting the edge of a field of radiation;

FIGS. 8*a* and 8*b* schematically illustrate two alternative implementations of the detection device, controller and phantom;

FIGS. 9*a*, 9*b* and 9*c* illustrate exemplary phantoms; and

Figure 10:
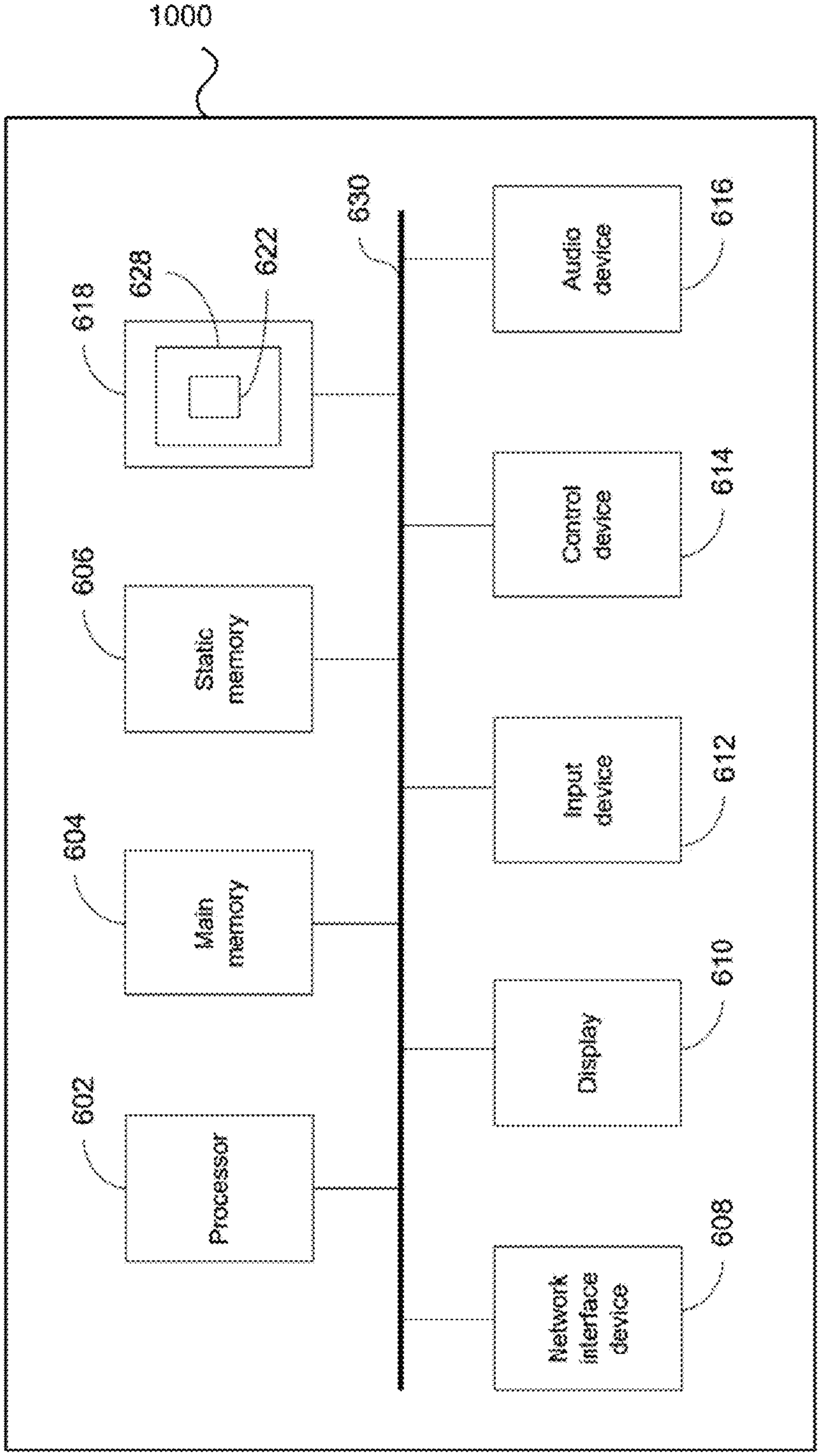

FIG. 10 depicts a block diagram of a computing device.

DETAILED DESCRIPTION

Overview

Aspects of the disclosure will be described below. In overview, and without limitation, the present application relates to providing a radiotherapy apparatus comprising a detector device which is adapted to work with a complementary phantom. The detector device can detect the position of the phantom using an optimised arrangement of detectors. This may provide a significant cost saving compared to currently used detector panels which use a large number of diodes (or ionisation chambers) to act as pixels for imaging a phantom. The detector device can be provided as part of a treatment system, and allow alignment of an imaging system with the treatment system.

Figure 1:
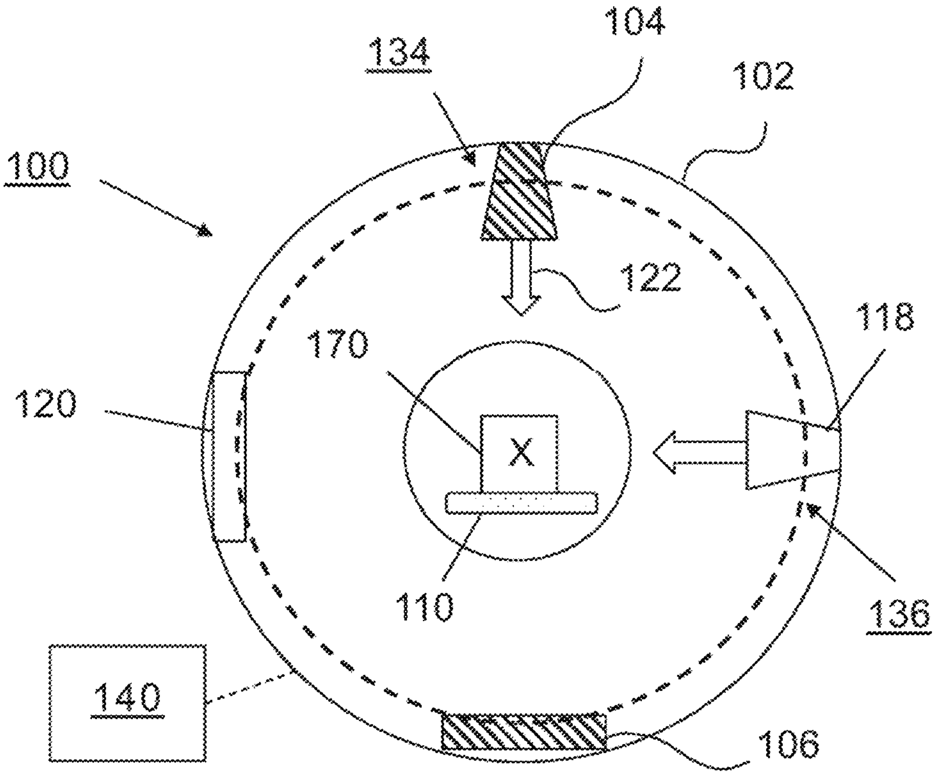
FIG. 1 depicts a radiotherapy device or apparatus according to the present disclosure.

FIG. 1 is a view of an exemplary radiotherapy apparatus 100. Radiotherapy apparatus 100 is, for example, an Image Guided Radiotherapy (IGRT) device comprising a linear accelerator (LINAC).

The radiotherapy apparatus 100 includes a gantry 102, which supports a treatment system 134 and an imaging system 136. In this example, the treatment system 134 and the imaging system 136 are attached to the gantry 102, so that they are rotatable with the gantry 102, e.g. so that they rotate as the gantry 102 rotates. Positioned generally along an axis 'X' central to the gantry is a couch 110 upon which a patient lies, for radiotherapy treatment. The couch 110 may be referred to as a 'patient support surface'.

The treatment system 134 includes a radiation head 104 and a detection device 106 (also referred to as a detection device, radiation detection device, detector system). The treatment system 134 may be, for example, a MV radiation treatment system. The radiation head 104 and the detection device 106 are mounted opposite each other on the gantry 102, with a rotational axis of gantry 102 positioned between them. The radiation head 104 is configured to generate a radiation beam 122 according to a treatment plan to deliver doses of radiation to a patient (or subject) supported by the couch 110. The gantry 102 is configured to rotate the radiation head 104 and detection device 106 about the couch 110, to provide patient with a plurality of varying dosages of radiation according to the treatment plan.

The detection device 106 is disposed such that it can detect the radiation beam after it has passed through the couch 110, in a similar way to a portal imaging device. However, unlike existing portal imaging devices, the detection device 106 is specifically optimised for beam QA procedures.

The radiation head 104 includes radiation source and a beam shaping apparatus (for example a collimator and/or MLC) for shaping the radiation beam 122. The radiation head 104 provides a beam of therapeutic radiation which may, for example, be in the megavoltage (MV) range.

The radiation beam 122 has a beam axis and a beam profile. The radiation beam axis may be defined by the geometry of the radiotherapy apparatus, for example the geometric centre of the beam (e.g. the centre of the radiation field which is the "window" defined by the beam shaping apparatus). The beam profile is the intensity distribution of the radiation on a plane perpendicular to the radiation beam axis.

The imaging system 136 comprises an imaging beam source 118 and an imaging panel 120. The imaging system may be, for example, a cone beam computed tomography (CBCT) system. The imaging beam source 118 is configured to emit and/or direct imaging radiation, for example X-rays and/or kV energy radiation, towards the patient. The imaging beam source 118 may be an X-ray tube or another suitable source of X-rays. The imaging beam source is configured to produce kV energy radiation. Once the imaging radiation has passed from the imaging beam source 118 and through the patient, the radiation continues towards the imaging panel 120. The imaging panel 120 is configured to produce signals indicative of the intensity of radiation incident on the imaging panel 120. In use, these signals are indicative of the intensity of radiation which has passed through the patient. These signals 50 may be processed to form an image of the patient. This process may be described as the imaging system 136 and/or the imaging panel 120 capturing an image. By capturing two-dimensional (2D) images at multiple angles around the patient, and combining them, it is possible to produce a 3D image of the patient, for example using tomographic reconstruction techniques.

In FIG. 1, the treatment system 134 and the imaging system 136 are mounted on the gantry 102 such that a treatment beam travels in a direction that is generally perpendicular (i.e. at right angles) to that of the imaging beam. However other relative positions of treatment system and imaging system are contemplated.

FIG. 1 also shows a phantom 170 which is positioned on the couch 110 of the radiotherapy apparatus 100. The phantom 170 and the radiotherapy apparatus 100 are specifically configured to work in a complementary way, allowing quality assurance procedures to be carried out without requiring the use of additional QA devices.

The detection device 106 includes detectors which are arranged to detect one or more edges of the phantom 170 in order to determine the position of the phantom 170. Each detector is configured to provide a measurement an overlap of a shadow cast by the phantom 170 on the respective detector when the radiation beam 122 is applied to the phantom 170 by the radiation head 104.

The radiotherapy apparatus 100 includes a controller 140 configured to receive the measurements from the detectors of the detection device 106 and to determine a position of the phantom 170 in a first coordinate system (e.g. the coordinate system of the treatment system 134) based on the measurements.

The controller may be programmed to control one or more of the treatment system 134, imaging system 136, couch 110 and the gantry 102. Controller 140 may perform functions or operations such as treatment planning, treatment execution, image acquisition, image processing, motion tracking, motion management, and/or other tasks involved in a radiotherapy process.

The controller 140 may be programmed to control features of the apparatus 100 according to a radiotherapy treatment plan for irradiating a target tissue of a patient. The treatment plan includes information about a particular dose to be applied to a target tissue, as well as other parameters such as beam angles, dose-histogram-volume information, the number of radiation beams to be used during therapy, the dose per beam, and the like. The controller 140 is programmed to control various components of apparatus 100—such as gantry 102, radiation head 104, detection device 106 and couch 110—according to the predetermined treatment plan.

The radiotherapy apparatus 100 has an isocentre. In an ideal system, the isocentre can be thought of as the point in space created by the intersection of the gantry rotation axis and the plane which is contains the trajectory of the radiation emitted by the source. This point serves as the geometric origin for the modelling of the radiation delivery in any treatment planning system and any patient imaging system. It is important to position a patient within the radiotherapy apparatus with knowledge of the position of the isocentre, and its position with respect to the target region. However, due to various effects (e.g. mechanical shifting or flexing as a function of gantry angle), the position of the radiation beam as defined by the beam shaping apparatus may also vary slightly with respect to this ideal isocentre as the apparatus is rotated.

The controller 140 is configured to control QA procedures for the radiotherapy apparatus 100, by controlling the radiation head 104 and the detection device 106.

The detection device 106 and controller 140 are adapted to measure therapeutic radiation emitted by the radiation head 104. Detectors of the detection device 106 are specifically adapted to provide radiation intensity data in order to allow calibration, QA and other procedures to be performed.

The detection device 106 advantageously includes an arrangement of detectors which allows QA procedures to be carried out, while minimising complexity and cost of the detection device itself. Additionally, the detection device 106 is integrated into the radiotherapy apparatus 100—being supported by the gantry 102 and connected to the controller 140. The detection device 106 can make measurements of the beam for QA purposes, where a patient is not generally present, and can also make measurements of the beam during a radiotherapy treatment, where a patient is present on the couch 110. The controller 140 can receive these measurements from the detection device 106 for use in QA procedures and, for example, dosimetry procedures. These 'exit dose' dosimetry measurements can be cross checked to what is expected based on the treatment plan.

The detection device 106 provides an optimised layout of detectors in order to reduce cost. Additionally, the controller 140 can be configured to control the beam shaping apparatus and the detection device 106 in order to perform QA and calibration. For QA where a patient is not present, dose is not an issue and therefore the detector can be less efficient.

The detection device 106 and the radiation head 104 may be provided in a fixed spatial configuration relative to one another (e.g. by being mounted to opposing sides of the rotatable gantry 102). This advantageously means that it is not necessary to manually position the detection device 106 in order to perform QA procedures.

Advantageously, the detection device can be more resistant to radiation as it includes fewer active components compared to existing integrated panel detectors. Where the detectors include ionisation chambers, these can be minimally affected by the total dose received. Also, the cost of the detection system can be so low that it is economic to replace it on a periodic basis. The detectors may be individually replaceable.

Detection Device

Figure 2:
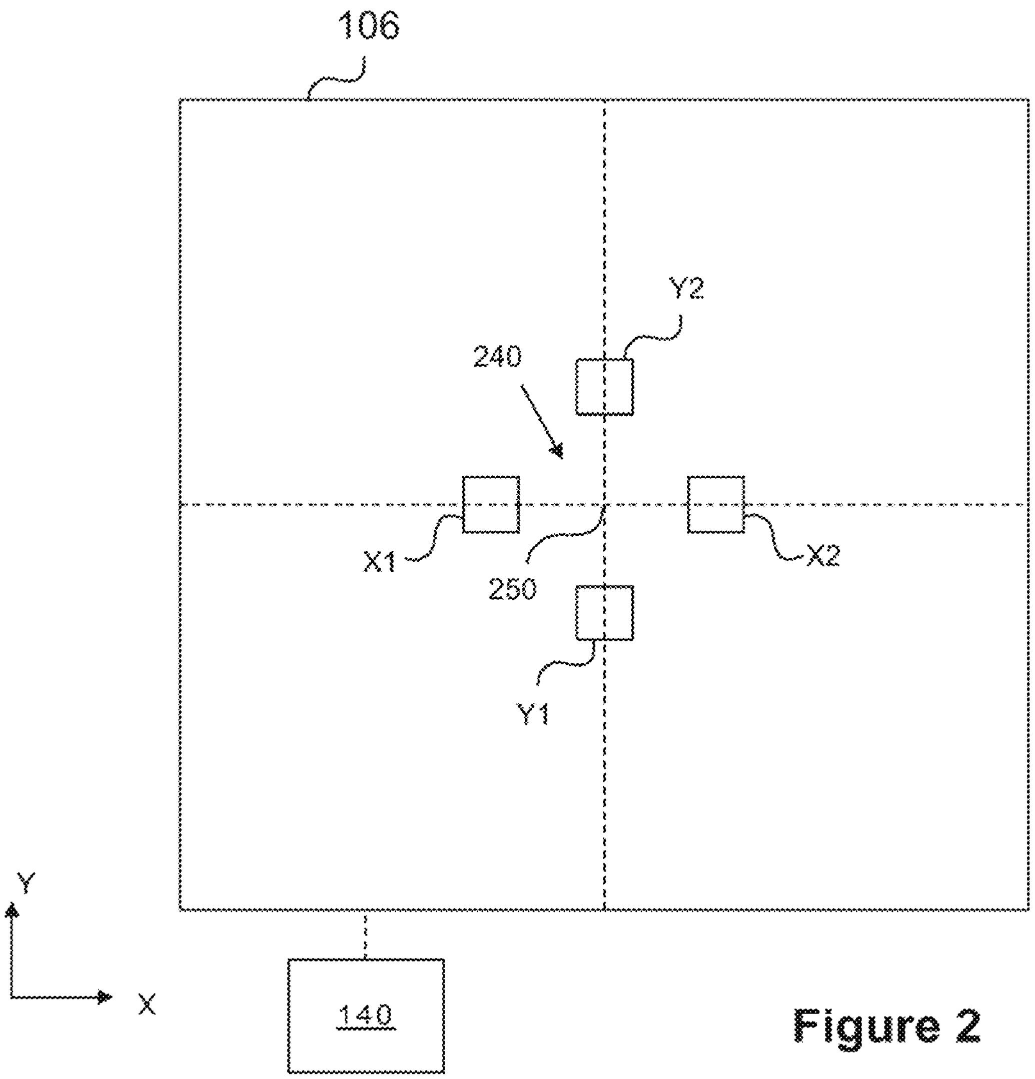
FIG. 2 illustrates an embodiment of a detection device for the radiotherapy apparatus of FIG. 1.

FIG. 2 illustrates an embodiment of the detection device 106 for the radiotherapy apparatus 100. This Figure shows the detection device 106 in the xy plane, where the beam axis (e.g. the z axis) goes into the page.

The detection device 106 includes four detectors (also referred to as sensors) X1, X2, Y1, Y2 which are each configured to provide a measurement of an overlap of a shadow cast by the phantom 170 on the respective detector when the radiation beam 122 is applied to the phantom 170. Each detector is configured to measure radiation incident on it, and the detectors are positioned in order to detect an edge of the shadow cast by the phantom 170.

In order for each detector to detect the edge of the shadow, the distance between centres of opposing detectors may configured to correspond to a width of the shadow. Furthermore, the phantom may be configured (and/or configurable) to match the spacing of the detectors.

Each detector X1, X2, Y1, Y2 may comprise a diode for detecting radiation, for example a photodiode, or an ion chamber or the like.

The detectors X1, X2, Y1, Y2 can be arranged around a non-detecting region 240 of the detection device 106. The non-detecting region is located at a central point 250 of the detection device 106. The non-detecting region 240 is substantially aligned with an isocentre of the radiotherapy apparatus, as the central point 250 is aligned with the projection of the isocentre of the treatment system 134. This may be an assumed isocentre of the treatment system 134, for example corresponding to an alignment marker of the radiotherapy system 100 which used to approximately identify the isocenter of treatment system 134.

The detectors X1, X2 form a first pair arranged to detect opposing edges of the shadow cast by the phantom. The controller 140 is configured to determine the position of the phantom 170 in the X dimension of the treatment system coordinates based on the measurements from the pair of detectors X1, X2.

Similarly, the detectors Y1, Y2 form a second pair arranged to detect opposing edges of the shadow cast by the phantom. The controller 140 is configured to determine the position of the phantom 170 in the Y dimension of the treatment system coordinates based on the measurements from the pair of detectors Y1, Y2.

The controller 140 is connected to the detection device 106, in order to receive measurement signals from the detection device 106. The detection device 106 measures the intensity of radiation received at each detector X1, X2, Y1, Y2, and outputs corresponding signals to the controller 140 indicating the intensity of radiation at defined spatial positions on the detection device 106 (e.g. radiation signal vs. position in the xy plane).

In some embodiments, the controller determines that the phantom 170 is aligned with the isocentre of the treatment system 134 when the output signal from each detector is 50% of its maximum output (or another threshold). This indicates that the shadow extends half way across each detector.

Detection Device in Use

FIGS. 3*a*, 3*b*, 4*a* and 4*b* illustrate an example of the detection device 106 in use. Specifically, FIGS. 3*a* and 4*a* illustrate a shadow 271 of the phantom 170 projected onto the detection device 106.

FIG. 3*a* shows that the shadow 271 of the phantom 170 projected onto the detection device 106 has a width pd, where d is a width of the phantom 170 (e.g. a width of a cross section of the phantom) and where p is a coefficient which can be predetermined based on the characteristics of the radiotherapy apparatus. The pitch of the detectors is configured to complement the phantom, for example the pitch of opposing detectors is configured to substantially match the width of the projected shadow of the phantom on the detectors. Therefore in FIG. 3*a* the distance between centres of detectors X1 and X2 is pd, and also the distance between centres of detectors Y1 and Y2 is also pd, since the phantom 170 has a square shadow in this example.

In FIG. 3*a*, the phantom 170 is positioned at the isocentre (or assumed isocentre) of the treatment system 134. In this example, the four detectors X1, X2, Y1, Y2 are positioned on the detection device 106 such that the shadow 271 overlaps with half of each detector (or half of a detecting area of each detector) and therefore, as shown in FIG. 3*b*, each detector outputs 50% of its maximum output—where maximum output corresponds to no overlap, and minimum output corresponds to full overlap. In the example of FIGS. 3*a* and 3*b*, the controller 140 may receive the measurements from the detectors X1, X2, Y1, Y2 and determine that the phantom 170 is aligned with an isocentre of the treatment system 134.

In FIG. 4*a*, the phantom 170 is not positioned at the isocentre (or assumed isocentre) of the treatment system 134. In this example, the phantom 170 is displaced from the isocentre in both the X and Y directions. Since the shadow 271 has minimal overlap with detectors X1 and Y1, nearly the maximum amount of radiation is incident on these detectors. Therefore, as shown in FIG. 4*b*, detectors X1 and Y1 output almost their maximum measurement. In contrast, the shadow overlaps with the majority of detectors X2 and Y2. Therefore, FIG. 4*b* shows that these detectors output close to their minimum measurement. As explained in more detail below, the controller 140 can use these output measurements to determine a location of the shadow 271, and hence the phantom 170, on the XY plane. This may depend on a calibration method in which the output response of detectors is determined for different phantom positions.

Method of Calibrating Detection Device

FIG. 5 is a graph showing exemplary outputs from X1 and X2 detectors of the detection device 106. Each output represents a measurement value of the edge of the phantom (or a measurement of any feature of the phantom) projected to the respective detector.

The detection device 106 can be calibrated across the detectable range, in both the X and Y directions. In order to perform calibration in the X direction, the phantom is moved from a first (e.g. the minimum detectable) X position to a second (e.g. the maximum detectable) X position, either continuously or in discrete steps. At each measurement point, the radiation beam 122 is applied to the phantom from the radiation head 104, and the output from the X1 and X2 detectors is determined. It will be appreciated that calibration in the Y direction can be performed in a similar way.

As can be seen in FIG. 5, when the phantom is in position x=A, the X1 detector output is at a minimum as the shadow 271 completely overlaps with it, while the X2 detector output is at a maximum because the shadow 271 does not overlap with it, and therefore radiation is incident on all of the detector X2 (e.g. over all of the detecting area of X2).

When the phantom is in position x=B, the X1 detector output is at a maximum as the shadow 271 does not overlap with it, while the X2 detector output is at a minimum because the shadow 271 fully overlaps with the X2 detector.

In this example, as the x position of the phantom changes, the output of each detector changes in a deterministic linear way. For small displacements this can be approximated as a linear change and the relationship between an X1 detector output $U_1$ and the position of phantom in the x direction can be modelled as follows:

$$U_1=m_1x+c_1$$

Where $m_1$ is the gradient of the line and $c_1$ is the intersect.

Similarly, the relationship between an X2 detector output $U_2$ and the position of phantom in the x direction can be modelled as follows:

$$U_2=m_2x+c_2$$

In the example of FIG. 5, $m_1=-m_2$

It will be appreciated that in some implementations, the relationship between detector output and phantom position is only approximately linear for small displacements, but it remains a useful approximation to determine the misalignment of the phantom and the detector.

More generally, the relationship between the detector output $U_1$ and $U_2$ and the position of phantom in the x direction is given by the functions:

$$U_1=F(x)$$

$$U_2=G(x)$$

The functions F(x) and G(x) can be determined based on the measurements of outputs from the detectors X1, X2 as the phantom is moved from a first x position to a second x position.

Although FIG. 5 shows exemplary outputs from X1 and X2 detectors of the detection device 106, the outputs from the Y1 and Y2 detectors can be calibrated in a similar way, where the relationship between the Y1 and Y2 detector outputs $U_3$ and $U_4$ and the position of phantom in the x direction is given by the functions:

$$U_3=H(y)$$

$$U_4=J(y)$$

These functions can therefore be used to provide a mapping between a measured detector output and a corresponding phantom position in one dimension.

Geometric Accuracy QA Test

FIG. 6 sets out simplified method steps of an exemplary geometric accuracy QA test. Geometric accuracy tests assess how well the isocentre of the imaging system 136 agrees with the isocentre of the treatment system 134. Correct alignment of the patient depends on this agreement, and therefore these tests are important and may need to be performed daily.

In the geometric accuracy test, a structure, for example a spherical phantom, is imaged with the imaging system 136 and alignment with the treatment system 134 is checked. In some examples, the treatment beam is detected from multiple angles to identify the isocentre of treatment system 134.

The test uses a phantom that comprises a structure which can be well imaged with the imaging system 136 and also easily detected using the detection device 106 of the treatment system 134.

At step 601, the phantom is first positioned on the radiotherapy apparatus, being lined up manually with an alignment marker of the radiotherapy system 100 which is used to approximately identify the isocentre of treatment system 134. The alignment marker may, for example, comprise a marking such as a cross hair on the couch 110 and/or may comprise alignment lasers.

At step 603, an imaging procedure is performed first, using the imaging system 136. Agreement of the imaged centre of the phantom may be checked against the centre of the image, as predefined in the imaging system 136.

In some examples, the phantom is iteratively imaged by the imaging system 136, moved, and re-imaged, until satisfactory alignment of the phantom with the imaging system 136 centre has been achieved (for example within 1 mm). In other examples, the position of the centre of the phantom as measured by the imaging system 136 is simply obtained, without subsequently moving and re-imaging the phantom. The phantom may be imaged at one or more gantry angles.

Next, at step 605, the position of the phantom 170 according to the treatment system 134 is determined. The phantom is irradiated with the treatment beam at one or more gantry angles—for example 0°, 90°, 180°, and 270°. The shadow cast by the phantom is detected, using the detection device 106, at each gantry angle. For example, the detection device 106 provides a data set based on measurements performed by each of the individual detectors of the detection device 106.

At step 607, the position of the phantom 170 is determined from the measurements output by the detectors of the detection device 106. For example, a set of functions mapping detector output to phantom position can be used, such as those described above.

At step 609, the phantom position measured by the treatment system 134 is compared to the phantom position measured by the imaging system 136. Effectively, the phantom position has been determined in two different coordinate systems—a first coordinate system corresponding to the imaging system 136, and a second coordinate system corresponding to the treatment system 136. Comparing the two measured phantom positions allows a determination of whether the two coordinate systems are aligned to a satisfactory threshold, and optionally allows the coordinate systems to be registered with one another, e.g. by applying calibration to the software instructions controlling the treatment system 134 and/or imaging system 136.

If the positions measured in the two systems are within a threshold (for example if the measured centre of the phantom is within 1 mm) then the geometric accuracy QA test is deemed to have been passed. In some examples, a notification is provided to a user as to whether the QA test has been passed, such as on a graphical user interface connected to the control system 140.

In some cases, in addition to or instead of step 609, the imaging system is registered with the radiation delivery system by applying a calibration based on the difference between the phantom position measured by the treatment system 134 and the phantom position measured by the imaging system 136.

For example, using the difference between the phantom positions, offset information can be obtained, which may be a 3D vector that indicates a shift required in order to align the imaging system with the radiation delivery system (this may be known as registration).

Detection Device Including Field Edge Detection

FIG. 7 illustrates an embodiment of a detection device 706 which includes additional detectors for detecting the edge of a field of radiation produced by the radiation beam 122.

The detection device 704 includes four detectors 710 which correspond to the four detectors X1, X2, Y1, Y2 described previously with reference to FIG. 2. These detectors 710 are arranged to provide a measurement an overlap of a shadow 771 cast by the phantom 170 on the respective detector when the radiation beam 122 is applied to the phantom 170.

The detection device also includes four edge detectors 712 which are positioned in order to detect an edge of the radiation field 760. FIG. 7 shows a projection of the radiation field 760 on the detection device. Each of the edge detectors 712 is arranged to provide a measurement an overlap of the radiation field 760 on the respective edge detector when the radiation beam 122 is applied by the radiation head 104.

The edge detectors can be configured in a similar way to the detectors X1, X2, Y1, Y2 by calibrating the edge detectors 712 based on measurements taken when the radiation field is in different positions. In order to perform calibration in the X direction, the edge of the radiation field 760 is moved from a first (e.g. the minimum detectable) X position to a second (e.g. the maximum detectable) X position, either continuously or in discrete steps. The whole radiation field can be moved, or the edge of the radiation field being measured can be moved—for example using the beam shaping apparatus. At each measurement point, the output from the detectors 712 is determined (or just the output from the detector(s) at the field edge being moved). It will be appreciated that calibration in the Y direction can be performed in a similar way.

As a result of the calibration, the relationship between the location of the edge of the radiation field 760 and the output of each detector 712 can be determined—for example resulting in one or more functions similar to those described above. The controller 740 can therefore map the output of each detector 712 to a radiation field edge position.

The detection device 706 can be used to test the position of the phantom with respect to the radiation field. In an exemplary test, the phantom is irradiated with the treatment beam at one or more gantry angles. The shadow cast by the phantom is detected, using the detectors 710, at each gantry angle. Additionally, the edge of the radiation field is detected by each of the detectors 712 for each gantry angle. Then, the position of the phantom 170 with respect to the edge of the radiation field 760 is determined from the measurements output by the detectors 710, 712 of the detection device 706. For example, a set of functions mapping detector output to phantom position and detector output to field edge position can be used.

Detection Device and Spherical/Cylindrical Phantom

FIGS. 8*a* and 8*b* schematically illustrate two alternative implementations of the detection device, controller and phantom. These implementations are adapted for use with a phantom having a circular cross section 870—for example a spherical or cylindrical phantom.

FIG. 8*a* shows detection device 806 which comprises four detectors 810 having a similar layout to the detection device described above. In this implementation, the controller 840 is configured to determine a phantom position based on the measurements obtained by the detectors 810, where the function defining the output for each detector depends on the position of the phantom in the x and y directions. This can be shown as follows:

$$U_1=F(x,y)$$

$$U_2=G(x,y)$$

$$U_3=H(x,y)$$

$$U_4=J(x,y)$$

FIG. 8*b* shows a detection device 856 which comprises three detectors 815. This implementation operates in a similar way to the detection device 806 in FIG. 8*a*, where the function defining the output for each detector also depends on the position of the phantom in the x and y directions.

Complementary Phantom

FIGS. 9*a*, 9*b* and 9*c* illustrate exemplary phantoms 970, 971 and 972 which can be used with the detection device. FIG. 9*a* illustrates a cubic phantom 970, with a width d, which casts a square shadow with width pd when projected onto the detection device, using the radiation beam.

FIG. 9*b* illustrates a spherical phantom 971 with diameter d, which casts a circular shadow with width pd when projected onto the detection device.

Although it has been described that the edge of the phantom is detected, it will be appreciated that any feature in the phantom that can be imaged can be used instead—this could be slots, plates etc. In all cases, the detectors of the detection device are configured to detect a projection of a feature of the phantom at the respective detector when a beam of radiation is applied to the phantom. This may include, for example, detecting a projection of a slot (e.g. detecting overlap of the slot) which is characterised by a greater intensity of radiation since less radiation is absorbed by the slot feature of a phantom.

FIG. 9*c* illustrates a cubic phantom 972, with a width greater than d, which includes a plate 980 on a front face of the cube, where the plate 980 has a width d. The plate 980 casts a square shadow with width pd when projected onto the detection device, using the radiation beam. The cubic phantom 972 may include one or more additional plates—for example the cubic phantom 972 may include a matching plate on an opposite, rear face, so that both plates cast a similar sized and positioned shadow on the detection device.

MODIFICATIONS AND ALTERNATIVES

Any implementations, examples, embodiments and the like described herein can be combined.

It will be understood that the description of specific implementations, examples, embodiments and the like is by way of example only and is not intended to limit the scope of the present disclosure. Many modifications of the described embodiments, some of which are now described, are envisaged and intended to be within the scope of the present disclosure.

Overview—Radiotherapy Apparatus

In some implementations, the radiotherapy apparatus 100 is a combination magnetic resonance imaging (MRI) and linear accelerator.

The radiation head 104 may comprise a heavy metal target towards which high energy electrons are directed. When the electrons strike the target, X-rays are produced in a variety of directions. A primary collimator (not shown) may block X-rays travelling in certain directions and pass only forward travelling X-rays to produce a treatment beam. The X-rays may be filtered and may pass through one or more ion chambers for dose measuring. In some implementations, the source of radiation is configured to emit either an X-ray beam or a particle beam. Such implementations allow the device to provide particle beam therapy, i.e. a type of external beam therapy where particles (e.g. protons or light ions), rather than X-rays, are directed toward the target region.

In some examples, the radiation source and the beam shaping apparatus are provided as a single unit, or alternatively the radiation source and the beam shaping apparatus may be provided separately.

It will be appreciated that the gantry may be replaced with one or more apparatus which allows the radiation head and the beam receiving apparatus to rotate around an axis of rotation.

The detection device may also be described as a detection device, radiation detecting means or detector system.

The detection device may be formed as a detection panel.

The detection device may not be unitary—for example it may include distributed components.

In some embodiments, the detection device is not used for patient imaging, and may not be used at all when a patient is undergoing radiotherapy.

The detection device is preferably provided as an integrated detector, for example in place of an EPID.

Detection Device

The detection device can include only two detectors, e.g. X1 and Y1. This can work particularly well with a phantom having a square/rectangular cross section (e.g. casting a square/rectangular shadow) because the function of the X1 output generally only depends on x position, and the function of the Y1 output generally only depends on y position.

The position of each detector may configurable in order to complement phantoms having different physical characteristics. For example, the pitch of detectors (e.g. distance between opposing detectors) may be adjustable, e.g. such that a pitch of the detectors corresponds to a distance between projected features of the phantom.

Geometric Accuracy QA Test

The phantom may include interchangeable elements—for example, a phantom which can be adapted to support interchangeable spherical structures which comprise different materials (e.g. a plastic ball and a metal ball). The phantom can be set up with such different elements depending on the procedure being performed—for example a plastic (e.g. lucite) ball can be optimally imaged using a kV CBCT, and a metal (e.g. tungsten) ball can be optimally detected using an MV treatment beam.

One example of a phantom which is well suited to a combination magnetic resonance imaging and linear accelerator (MR-linac) is uses a combination of Zirconium balls surrounded by oil.

In some examples, the phantom position measured by the treatment system 134 is checked against a centre of the detection area of the detection device, as predefined in the treatment system 134.

In one example, a CT image of the phantom is used to provide an imaging data set. In order to create such data set, the phantom may be scanned with a CT scanner using a thin slice thickness of 1 or 1.5 mm. The CT data set is then sent to the treatment planning system, where the isocentre is carefully located and marked.

Although FIG. 6 shows that the phantom position is first determined with the imaging system and then with the treatment system, the test can also be performed in a different order. In some cases it is preferable that the position of the phantom is firstly moved iteratively to align with the radiotherapy apparatus, using the detection device, and then the phantom is imaged by the imaging system. The imaging system is more able to measure the misalignment of the phantom with the imaging system as it has a high spatial resolution.

In some examples, the data set obtained by the treatment system 134 and/or the imaging system 136 is sent to a treatment planning system, which is configured to determine a position of the phantom.

In an implementation, the phantom may be placed at or substantially at the treatment isocentre, and a full 360-degree scan (or single scan) is performed by the treatment system. If it is determined, from the measurements taken, that the phantom is not positioned at the treatment isocentre, then the phantom is moved, and the full 360-degree scan is performed again. This process is repeated until it is determined, from the measurements taken, that the ball-bearing phantom is located at the treatment isocentre, or the 'averaged' treatment isocentre.

Controller

The controller can be provided by multiple separate controllers (separate in hardware and/or software), and may include distributed components.

Hardware components of controller may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

FIG. 10 illustrates a block diagram of one implementation of a computing device 1000 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 1000 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a secondary memory (e.g., a data storage device 618), which communicate with each other via a bus 630.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 622) for performing the operations and steps discussed herein.

The computing device 1000 may further include a network interface device 608. The computing device 1000 also may include a video display unit 610 (e.g., a liquid crystal display (LCD) or a cathode ray tube (CRT)), an alphanumeric input device 612 (e.g., a keyboard or touchscreen), a cursor control device 614 (e.g., a mouse or touchscreen), and an audio device 616 (e.g., a speaker).

The data storage device 618 may include one or more machine-readable storage media (or more specifically one or more non-transitory computer-readable storage media) 628 on which is stored one or more sets of instructions 622 embodying any one or more of the methodologies or functions 50 described herein. The instructions 622 may also reside, completely or at least partially, within the main memory 604 and/or within the processing device 602 during execution thereof by the computer system 1000, the main memory 604 and the processing device 602 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-RAN or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A detection device for a radiotherapy apparatus, the detection device comprising:
- an arrangement of detectors comprising a plurality of radiation detectors, wherein the plurality of detectors are arranged around a non-detecting region of the detection device, and wherein each respective detector of the plurality of radiation detectors is arranged and configured to:
  - detect a projection of a feature of a phantom at the respective detector when a beam of radiation is applied to the phantom; and
  - output a measurement value based on the detected projection; and
- a controller configured to:
  - receive the measurement value from each respective detector of the plurality of detectors; and
  - determine a position of the phantom in a first coordinate system based on the received measurement values.

2. The detection device of claim 1, wherein the position of the phantom is determined based on a predetermined relationship between phantom position and the measurement values from each respective detector of the plurality of radiation detectors.

3. The detection device of claim 2, wherein the predetermined relationship is based on a calibration between phantom position and the measurement values.

4. The detection device of claim 1, wherein each respective detector corresponds to a single pixel.

5. The detection device of claim 1, wherein the measurement value is a measurement of an overlap of the feature of the phantom on a particular respective detector.

6. The detection device of claim 1, wherein the feature is an edge of a shadow cast by the phantom.

7. The detection device of claim 1, wherein the plurality of detectors are arranged such that each respective detector can detect a projected feature of the phantom when the phantom is at an isocentre of the radiotherapy apparatus.

8. The detection device of claim 1, wherein the plurality of detectors are arranged with a pitch that corresponds to a distance between the projected features of the phantom.

9. The detection device of claim 1, wherein the non-detecting region of the detection device is located at a central point of the detection device, and wherein a distance between centers of opposing detectors of the plurality of detectors corresponds to a width of a projected shadow of the phantom on the detection device.

10. The detection device of claim 1, wherein the non-detecting region is substantially aligned with a projected isocentre of the radiotherapy apparatus.

11. The detection device of claim 1, wherein a first pair of detectors of the plurality of detectors are arranged to detect opposing projected features of the phantom, and wherein the controller is configured to determine the position of the phantom in a first dimension of a first coordinate system based on the measurements from the first pair of detectors.

12. The detection device of claim 11, wherein a second pair of detectors of the plurality of detectors are arranged to detect opposing projected features of the phantom, and wherein the controller is configured to determine the position of the phantom in a second dimension of the first coordinate system based on the measurements from the second pair of detectors.

13. The detection device of claim 1, wherein the position of each detector is configurable to complement phantoms having different physical characteristics.

14. The detection device of claim 1, wherein the controller is configured to:

determine a position of the phantom in a second coordinate system using an imaging apparatus; and compare the phantom position in the first coordinate system to the phantom position in the second coordinate system.

15. A radiotherapy apparatus comprising:

a radiation source configured to emit a beam of radiation; and a detection device including:

an arrangement of detectors comprising a plurality of radiation detectors, wherein the plurality of detectors are arranged around a non-detecting region of the detection device, and wherein each respective detector of the plurality of radiation detectors is arranged and configured to:

detect a projection of a feature of a phantom at the respective detector when a beam of radiation is applied to the phantom; and output a measurement value based on the detected projection; and a controller configured to:

receive the measurement value from each respective detector of the plurality of detectors; and determine a position of the phantom in a first coordinate system based on the received measurement values.

16. The detection device of claim 1, wherein the detection device is included in a kit, and wherein the kit comprises:

a complementary phantom configured such that each detector of the detection device detects a projected feature of the phantom when the phantom is at an isocentre of the radiotherapy apparatus and a beam of radiation is applied to the phantom.

17. A method of determining a position of a phantom in a radiotherapy system, the method comprising:

receiving a measurement value, from each respective detector of a plurality of radiation detectors of an arrangement of detectors, wherein the plurality of detectors are arranged around a non-detecting region of a detection device, of a projection of a feature of a phantom at each respective detector when a beam of radiation is applied to the phantom, each respective detector being arranged to detect the projection of the feature of the phantom when the beam of radiation is applied to the phantom; and determining the position of the phantom in a first coordinate system based on the received measurement value from each respective detector.

18. The method of claim 17, wherein the position of the phantom is determined based on a predetermined relationship between phantom position and the received measurement value from each respective detector of the plurality of radiation detectors.

19. The method of claim 18, wherein the predetermined relationship is based on a calibration between the position of the phantom position and measurement value from each respective detector of the plurality of radiation detectors.

20. The method of claim 17, wherein each measurement value from each respective detector of the plurality of radiation detectors corresponds to a single pixel.

21. The method of claim 17, further comprising:

determining a position of the phantom in a second coordinate system using an imaging apparatus; and comparing the phantom position in the first coordinate system to the phantom position in the second coordinate system.

22. The method of claim 17, wherein the measurement value is a measurement of an overlap of the feature of the phantom on the respective detector.

23. The method of claim 17, wherein the feature is an edge of a shadow cast by the phantom.

24. The method of claim 17, wherein a non-transitory computer-readable medium that stores instructions which, when executed by one or more processors of a computer device, cause the computer device to perform the method.

* * * * *